US005620959A

United States Patent [19]
Leban et al.

[11] Patent Number: 5,620,959
[45] Date of Patent: Apr. 15, 1997

[54] BOMBESIN ANTAGONISTS

[75] Inventors: Johann J. Leban, Kittsee, Austria; Frederick C. Kull, Durham, N.C.

[73] Assignee: Glaxo Wellcome Inc., Research Triangle Park, N.C.

[21] Appl. No.: 344,797

[22] Filed: Nov. 23, 1994

Related U.S. Application Data

[63] Continuation of Ser. No. 972,447, Jan. 29, 1993, abandoned.

[30] Foreign Application Priority Data

Jul. 31, 1990 [GB] United Kingdom ............... 9016810

[51] Int. Cl.$^6$ ..................... A61K 38/00; C07K 7/06; C07K 7/08
[52] U.S. Cl. .................. 514/16; 514/14; 514/15; 514/17; 514/13; 530/327; 530/326; 530/328; 530/329
[58] Field of Search ............... 530/326–329; 514/13–16, 17

[56] References Cited

U.S. PATENT DOCUMENTS

| | | | |
|---|---|---|---|
| 4,767,628 | 8/1988 | Hutchinson | 514/12 |
| 4,943,561 | 7/1990 | Heimbrook et al. | 530/329 |
| 5,004,602 | 4/1991 | Hutchinson | 424/78 |
| 5,019,647 | 5/1991 | Riemen et al. | 530/329 |
| 5,047,502 | 9/1991 | Oliff et al. | 530/329 |
| 5,084,555 | 1/1992 | Coy et al. | 530/328 |
| 5,100,873 | 3/1992 | de Castiglione et al. | 530/329 |

FOREIGN PATENT DOCUMENTS

| | | |
|---|---|---|
| 0345990 | 12/1989 | European Pat. Off. |
| WO91/04040 | 4/1991 | WIPO |

OTHER PUBLICATIONS

Coy, et al, J. Biol Chem, vol. 263, No. 11, pp. 5056–5060. 1988.

Martinez, et al, J. Med. Chem. 28, pp. 1874–1879, 1985.

Mahmond, S. et al., "[Psi$^{13,14}$] Bombesin Analogues Inhibit Growth of Small Cell Lung Cancer in Vitro and in Vivo$^1$", *Cancer Research*, 51, 1798–1802 (1991).

Mahmoud, S. et al., "Small Cell Lung Cancer Bombesin Receptors are Antagonized by Reduced Peptide Bond Analogues", *Life Sciences*, 44, 367–373 (1989).

Woll, P. et al., "[D–Arg$^1$,D–Phe$^5$, D–Trp$^{7,9}$, Leu$^{11}$]substance P, a potent bombesin antagonist in murine Swiss 3T3 cells, inhibits the growth of human small cell lung cancer cells in vitro", *Proc. Natl. Acad. Sci.*, 85, 1859–1863 (1988).

Coy, D.H. et al., "Probing Peptide Backbond Function in Bombesin", *J. Biological Chemistry*, 263(11), 5056–5060 (1988).

Tourwe, D. et al., "synthesis and Biological Activity of Bradykinin Analogues with Reduced and Ethylenic Isosteric Peptide Bond Replacements", *Peptides*, 562–7 (1988).

Dung Le–Nguyen et al., "Renin Substrates. Part 2. $^1$ Rapid Solid Phase synthesis of the Ratine Sequence Tetradecapeptide Using BOP Reagent", *J. Chem. Soc. Perkin Trans. I*, 1915 (1987).

Martinez, J. et al., "Synthesis and Biological Activities of Some Pseudo–Peptide Analogues of Tetragastrin: The Importance of the Peptide Backbone", *J. Med. Chem.*, 28, 1874–1879 (1985).

Walsh, J.H. et al., "Mammalian Bombesin–Like Peptides: Neuromodulators of Gastric Function and Autocrine Regulators of Lung Cancer Growth", *Peptides*, 6(3), 63–68 (1985).

Mancuso, A.J. et al., "Oxidation of Long–chain and Related Alcohols to Carbonyls by Dimethyl Sulfoxide Activated by Oxalyl Chloride", *J. Org. Chem.*, 43(12), 2480–2 (1978).

Sakakibara, S. et al., "Use of Anhydrous Hydrogen Flouride in Peptide Synthesis. I. Behavior of Various Protective Groups in Anhydrous Hydrogen Fluoride", *Bulletin of the Chem. Soc. of Japan*, 40(9), 2164–2167 (1967).

Merrifield, R.B., et al., "Solid Phase Peptide Synthesis. I. The Synthesis of a Tetrapeptide", *J. American Chemical Society*, 83, 2149–54 (1963).

*Primary Examiner*—Cecilia Tsang
*Assistant Examiner*—S. G. Marshall
*Attorney, Agent, or Firm*—Robert T. Hrubiec

[57] ABSTRACT

The present invention provides polypeptides of the formula $XX^1TrpX^2X^3X^4X^5X^6X^7NH_2$, methods of treatment using the polypeptides, pharmaceutical compositions comprising such polypeptides, and processes for their preparation. The polypeptides possess antagonist properties against bombesin and bombesin-like peptides and are useful in the treatment of malignant disease. M, X, $X^1$, $X^2$, $X^3$, $X^4$, $X^5$, $X^6$, and $X^7$ are as defined in the specification.

8 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
         Glu  Gln  Arg  Leu  Gly  Asn  Gln  Trp  Ala  Val  Gly  His  Leu  Met
          1         5              10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
         Gly  Asn  His  Trp  Ala  Val  Gly  His  Leu  Met
          1         5              10
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=VARIABLE
            / note="SELECTED FROM: see specification at page 3
            for a definition of this group."

( i x ) FEATURE:
        ( A ) NAME/KEY: Modified-site
        ( B ) LOCATION: 2
        ( D ) OTHER INFORMATION: /label=VARIABLE
            / note="SELECTED FROM: His, ThiAla or is deleted."

( i x ) FEATURE:
        ( A ) NAME/KEY: Modified-site
        ( B ) LOCATION: 4
        ( D ) OTHER INFORMATION: /label=VARIABLE
            / note="SELECTED FROM: Ala,
            CPenc(aminocyclopentanecarboxylic acid) or Pro."

( i x ) FEATURE:
        ( A ) NAME/KEY: Modified-site
        ( B ) LOCATION: 5
        ( D ) OTHER INFORMATION: /label=VARIABLE
            / note="SELECTED FROM: Val or Val substituted by
            one or more halo atoms."

( i x ) FEATURE:
        ( A ) NAME/KEY: Modified-site
        ( B ) LOCATION: 6
        ( D ) OTHER INFORMATION: /label=VARIABLE
            / note="SELECTED FROM: Gly, Ala, Sarcosine or
            Pro."

( i x ) FEATURE:
        ( A ) NAME/KEY: Modified-site
        ( B ) LOCATION: 7
        ( D ) OTHER INFORMATION: /label=VARIABLE
            / note="SELECTED FROM: His or ThiAla."

( i x ) FEATURE:
        ( A ) NAME/KEY: Modified-site
        ( B ) LOCATION: 8
        ( D ) OTHER INFORMATION: /label=VARIABLE
            / note="SELECTED FROM: Pro(CH2NH) or
            2- pyrrolidinyl-3-hydroxypropionyl."

( i x ) FEATURE:
        ( A ) NAME/KEY: Modified-site
        ( B ) LOCATION: 9
        ( D ) OTHER INFORMATION: /label=VARIABLE / note="SELECTED FROM: Nle, Leu, Phe, Val,
Mox(methoxinine), naphthyAla or a hydrophobic,
substituted aromatic amino acid or aralkylamine or is
deleted."

( x i ) SEQUENCE DESCRIPTION: SEQ ID NO:3:

Xaa Xaa Trp Xaa Xaa Xaa Xaa Xaa Xaa
1       5

BOMBESIN ANTAGONISTS

This is a continuation of application Ser. No. 07/972,447 filed on Jan. 29, 1993 now abandoned.

BACKGROUND OF THE INVENTION

The present invention relates to polypeptide compounds which possess antagonist properties against bombesin, or bombesin-like peptides, and are useful in the treatment of disease, particularly human small-cell lung cancer. Zollinger-Ellison syndrome or pancreatic cancer. The invention thus provides the polypeptides, processes for preparing them, pharmaceutical compositions containing them, and their use in medicine.

Bombesin is a tetradecapeptide originally isolated from the skin of a frog. It has the formula

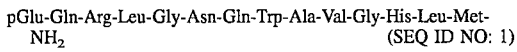

pGlu-Gln-Arg-Leu-Gly-Asn-Gln-Trp-Ala-Val-Gly-His-Leu-Met-NH$_2$ (SEQ ID NO: 1)

Gastrin releasing peptide is a 27 amino acid peptide isolated from the porcine gut. The last ten amino acids at the C-terminus of gastrin releasing peptide correspond with one amino acid alteration (3) to the last ten amino acids of bombesin, viz:

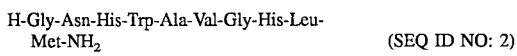

H-Gly-Asn-His-Trp-Ala-Val-Gly-His-Leu-Met-NH$_2$ (SEQ ID NO: 2)

It has been reported (J. H. Walsh and J. R. Reeve, Peptides 6, (3), 63–68, (1985)) that bombesin and bombesin-like peptides such as gastrin releasing peptide are secreted by human small-cell lung cancer (SCLC) cells. It has been postulated (P. J. Woll and E. Rozengurt, PNAS 85, 1859–1863, (1988)) that gastrin releasing factor antagonists would bind competitively to bombesin receptors in animals and would therefore be of use in the treatment of SCLC and/or in the control of clinical symptoms associated with this disease and due to hypersecretion of this peptide hormone. Analogues of bombesin have been shown to inhibit the binding of gastrin releasing peptide to a SCLC cell line and to inhibit the growth of SCLC cells in-vitro and in-vivo (S. Mahmoud et al., Cancer Research, 51, 1798–1802 (1991)).

Several bombesin antagonists have been disclosed, for example [Leu$^{13}$-ψ(CH$_2$—NH)-Leu$^{14}$] bombesin and [Ala$^9$-ψ(CH$_2$—NH)-Val$^{10}$Leu$^{14}$] bombesin (Coy et al, *J. Biol Chem.*, 1988, 263, 5056) and 4-Pyridyl-CO-His-Trp-Ala-Val-D-Ala-His-Leu-OMe,
4-Pyridyl-CO-His-Trp-Ala-Val-D-Ala-His-Leu-NHMe,
4-Pyridyl-CO-His-Trp-Ala-Val-D-Ala-His-MeLeu-OMe,
3-Pyridyl-CO-His-Trp-Ala-Val-D-Ala-His-MeLeu-OMe,
4-Pyridyl-CO-His-Trp-Ala-Val-D-Ala-Lys(Z)-MeLeu-OMe,
3-Indolyl-Co-His-Trp-Ala-Val-D-Ala-His-Leu-OMe,
4-Pyridyl-CO-His-Trp-Ala-Val-D-Ala-His-MeLeu-NHMe,
4-Pyridyl-CO-His-Trp-Ala-Val-D-Ala-Lys(Z)-Leu-NHMe,
4-Pyridyl-CO-His-Trp-Ala-Val-D-Ala-Lys(COCH$_2$Ph)-Leu-NHMe and
4-Pyridyl-CO-His-Trp-Ala-Val-D-Ala-Lys(COCH$_2$CH$_2$Ph)-Leu-NHMe.
(European Patent Application No. 345990A).

In the formula (I) below and throughout this specification, the amino acid residues are designated by their standard abbreviations (*Pure and Applied Chemistry*, 1974, 40, 317–331; *European Journal of Biochemistry*, 1984, 138, 9–37).

For the avoidance of doubt it is stated that: amino acid symbols denote the L-configuration unless otherwise indicated by D or DL appearing before the symbol and separated from it by a hyphen. (R) and (S) are the standard designations for molecular configuration.

The following abbreviations are used:
ψ=psi(CH$_2$NH)
Ada=1-adamantanecarboxylic acid
CPenc=aminocyclopentanecarboxylic acid
Mox=methoxinine
Des NH$_2$Pro=1-cyclopentanecarboxylic acid
Des NH$_2$Tyr=(4'-hydroxy)-3-phenylpropionic acid
ThiAla=3-(2-thienyl)-alanine
D-tBuGly=D-tertiary-butyl-glycine (tertiary-D-leucine)
When the Ada,CPenc,Mox,des NH$_2$Pro,des NH$_2$Tyr groups are in a polypeptide chain they are in the carbonyl form.

It has now been discovered that a further group of polypeptides have potent bombesin antagonist activity.

The compounds of the present invention inhibit the production of gastrin releasing peptide in mammalian cells and are therefore useful in controlling the clinical symptoms of diseases which cause the secretion of hypersecretion of gastrin releasing peptide (e.g., SCLC).

SUMMARY OF THE INVENTION

Accordingly, the present invention provides a polypeptide of the formula (I):

XX$^1$TrpX$^2$X$^3$X$^4$X$^5$X$^6$X$^7$NH$_2$ (I) SEQ ID NO: 3)

wherein X is a group X$^8$Arg(or D-Arg)X$^9$X$^{10}$ and X$^8$ is des NH$_2$Pro,TyrPro,des NH$_2$TyrPro, Ada, Pro, D-Pro or is deleted;

X$^9$ is Gly, Ala, D-Ala or is deleted;

X$^{10}$ is Asn, Phe, D-Phe, or Phe or D-Phe substituted by one or more halo atoms;

or X is a group A-(CH$_2$)$_n$—CO— in which A is a group containing 1 to 3 rings of which at least one ring is aromatic, each ring system being optionally substituted; and the alkylene group is optionally substituted by one to four groups selected from amino, hydroxy C$_{1-4}$ alkoxy and C$_{1-4}$ alkyl optionally substituted by halo and n is 0 to 4, or X is a group A-(CH$_2$)$_n$—CO— in which A is an optionally substituted aromatic residue containing 1 to 3 rings and the alkylene group is optionally substituted by one to four groups selected from amino, C$_{1-4}$ alkoxy and C$_{1-4}$ alkyl optionally substituted by halo and n is 1 to 4, or X is cyclopentylcarbonyl substituted by a group X$^8$ Arg (or D-Arg)

X$^9$ X$^{10}$ as hereinbefore defined;

X$^1$ is His, ThiAla or is deleted;

X$^2$ is Ala, D-Ala, CPenc, D-tBuGly or Pro;

X$^3$ is Val or Val substituted by one or more halo atoms;

X$^4$ is Gly, Ala, D-Ala, Sarcosine, Pro, D-Pro or D-Phe;

X$^5$ is His or ThiAla;

X$^6$ is D-Proψ, Proψ, 2-pyrrolidinyl-3-hydroxypropionyl or D-Pro;

X$^7$ is Nle,Leu,Phe,Val,Mox, D-Phe or Phe, or D-Phe substituted by one or more halo atoms or naphthylAla or naphthyl D-Ala or a hydrophobic, substituted aromatic amino acid or aralkylamine or is deleted.

3

Suitably A is phenyl, naphthyl, phenothiazinyl or indolyl. Preferably A is phenyl or naphthyl.

Suitable substituents for the aromatic ring Ar include hydroxy, phenyl, halo, $C_{1-4}$ alkyl or $C_{1-4}$ alkoxy optionally substituted by halo.

Preferably n is 2.

Suitably X terminates in a des $NH_2$ moiety.

Suitably $X^8$ is des $NH_2$Tyr or des $NH_2$Pro. Suitably $X^9$ is Gly or D-Ala.

Suitably $X^{10}$ is D-Phe. Preferably X is des $NH_2$Phe, des $NH_2$Tyr, des $NH_2$TyrPro (or D-Pro) Arg (or D-Arg).

Preferably $X^1$ is His or ThiAla;

Preferably $X^2$ is Ala, Pro;

Preferably $X^3$ is Val or hexafluorovaline;

Preferably $X^4$ is D-Ala, D-Phe;

Preferably $X^5$ is His, ThiAla;

Preferably $X^6$ is D-Proψ, Proψ, Pro, D-Pro;

Preferably $X^7$ is Nle or Phe, Leu, Methoxinine, 2-Naphthyl-2-Alanine.

Preferred polypeptides of the present invention include:
N-((R)-2-(6-Methoxy-2-Naphthyl)Propionyl)-HisTrpAlaValD-AlaHisD-ProψNle-NH$_2$
N-((S)-2-(6-Methoxy-2-Naphthyl)Propionyl)-HisTrpAlaValD-AlaHisD-ProψNle-NH$_2$
N-((S)-3-Phenylbutyryl)-HisTrpAlaValD-AlaHisD-ProψNle-NH$_2$
N-((R)-3-Phenylbutyryl)-HisTrpAlaValD-AlaHisD-ProψNle-NH$_2$
N-((3-Phenyl)Propionyl)-HisTrpAlaValD-Ala(3-(2-Thi)-Ala)D-ProψNle-NH$_2$
N-((S)-3,3,3-Trifluoro-2-Methoxy-2-Phenyl-Propionyl)-HisTrpAlaValD-ProψNle-NH$_2$
N-((R)-3,3,3-Trifluoro-2-Methoxy-2-Phenyl-Propionyl)-HisTrpAlaValD-ProψNle-NH$_2$
N-3-(((4'-Hydroxy)Phenyl)Propionyl)-ProD-ArgGlyD-PheHisTrpAlaValGlyHisD-ProψNle-NH$_2$
N-(((4'Hydroxy)-3-Phenyl)Propionyl)-ProD-ArgHisTrpAlaValD-AlaHisD-ProψLeu-NH$_2$
N-((3-Phenyl)Propionyl)-HisTrpAlaValD-AlaHisD-Proψmox-NH$_2$
N-((3-Phenyl)Propionyl)-HisTrpAlaValD-ProψPhe-NH$_2$
N-((3-Phenyl)Propionyl)-TrpAlaValD-AlaHisD-ProψLeu-NH$_2$
N-((3-Phenyl)Propionyl)-HisTrpProValD-ProHisD-ProψLeu-NH$_2$
N-3-(((3'-Trifluoromethyl)Phenyl)Propionyl)-HisTrpAlaValD-AlaHisD-ProψLeu-NH$_2$
N-((3-Phenyl)Propionyl)-(3-(2-Thi)-Ala)TrpAlaValD-AlaHisD-ProψLeu-NH$_2$
N-((deamino-Pro)-D-ArgD-AlaD-PheHisTrpAlaValGlyHisD-ProψNle-NH$_2$
N-((3-Phenyl)Propionyl)-HisTrpAlaValGlyHisD-ProψNle-NH$_2$
N-((deamino-Pro)-D-ArgD-AlaD-PheHisTrpAlaValD-AlaHisD-ProψNle-NH$_2$
N-((3-Phenyl)Propionyl)-HisTrpAlaValD-AlaHisD-ProψNle-NH$_2$
TyrProD-ArgGlyD-PheHisTrpAlaValGlyHisD-ProψNle-NH$_2$
D-ArgGlyD-PheHisTrpAlaValGlyHisD-ProψNle-NH$_2$
N-((3-Phenyl)Propionyl)-HisTrpAlaValD-AlaHisD-ProPhe-NH$_2$
N-((3-Phenyl)Propionyl)-HisTrpAlaValD-AlaHisD-Proψ(3-(2-Naphthyl)-D-Ala)-NH$_2$
N-((3-Phenyl)Propionyl)-HisTrpAlaValD-PheHisD-ProψPhe-NH$_2$

4

D-PheHisTrpAlaValD-AlaHisD-ProψPhe-NH$_2$
N-((3-Phenyl)Propionyl)-D-ProArgGlyD-PheHisTrpAlaValD-AlaHisD-ProψPhe-NH$_2$
N-((3-Phenyl)Propionyl)-(3-(2-Thi)-Ala)-TrpAlaValD-AlaHisD-ProψPhe-NH$_2$
N-((3-Phenyl)Propionyl)-HisTrpAlaVal-(Sarcosine)-HisD-ProψPhe-NH$_2$
N-3-(((4'-Hydroxy)Phenyl)Propionyl)-HisTrpAlaValD-AlaHisD-ProψPhe-NH$_2$
N-(((2',6'-Dichloro)-2-Phenyl)Acetyl)-HisTrpAlaValD-AlaHisD-ProψNle-NH$_2$
N(((3',4'-Dichloro)-2-Phenyl)Acetyl)-HisTrpAlaValD-AlaHisD-ProψNle-NH$_2$
N-(((4'-Hydroxy)-2-Phenyl)Acetyl)-HisTrpAlaValD-AlaHisD-ProψNle-NH$_2$
N-(1-Naphthoyl)-HisTrpAlaValD-AlaHisD-ProψNle-NH$_2$
N-((3,7-Dihydroxy)-2-Naphthoyl)-HisTrpAlaValD-AlaHisD-ProψNle-NH$_2$
N-((3,4-Dihydroxy)-2-Phenyl)Acetyl)-HisTrpAlaValD-AlaHisD-ProψNle-NH$_2$
N-(2-(3-Pyridyl)Acetyl)-HisTrpAlaValD-AlaHisD-ProψNle-NH$_2$
N-(2-(2-Thienyl)Acetyl)-HisTrpAlaValD-AlaHisD-ProψNle-NH$_2$
N-(((3-Fluoro)-3-Phenyl)Prop-ionyl)-HisTrpAlaValD-AlaHisD-ProψNle-NH$_2$
N-(((4-hydroxy-3-methoxy)-2-Phenyl)Acetyl)-HisTrpAlaValD-AlaHisD-ProψNle-NH$_2$
N-(((R)-(−)-2-Phenyl)Propionyl)-HisTrpAlaValD-AlaHisD-ProψPhe-NH$_2$
N-(((S)-(+)-2-Phenyl)Propionyl)-HisTrpAlaValD-AlaHisD-ProψPhe-NH$_2$
N-(((Trans)-2-Phenyl)-Cyclopro-panoyl)-HisTrpAlaValD-AlaHisD-ProψPhe-NH$_2$
N-(3-(10-Phenothiazinyl)Propionyl-HisTrpAlaValD-AlaHisD-ProψPhe-NH$_2$
N-((3-Methyl-3-Phenyl)Butyryl)-HisTrpAlaValD-AlaHisD-ProψPhe-NH$_2$
N-(((2'-Trifluoromethyl)-2-Phenyl)Acetyl)-HisTrpAlaValD-AlaHisD-ProψPhe-NH$_2$
N-(((3'-Trifluoromethyl)-2-Phenyl)Acetyl)-HisTrpAlaValD-AlaHisD-ProψPhe-NH$_2$
N-(((4'-Trifluoromethyl)-2-Phenyl)Acetyl)-HisTrpAlaValD-AlaHisD-ProψPhe-NH$_2$
N-(((2',3'-Difluoro)-2-Phenyl)Acetyl)-HisTrpAlaValD-AlaHisD-ProψPhe-NH$_2$
N-(((2',4'-Difluoro)-2-Phenyl)Acetyl)-HisTrpAlaValD-AlaHisD-ProψPhe-NH$_2$
N-(((2',6'-Difluoro)-2-Phenyl)Acetyl)-HisTrpAlaValD-AlaHisD-ProψPhe-NH$_2$
N-(((2-Amino)-2-Phenyl)Acetyl)-HisTrpAlaValD-AlaHisD-ProψPhe-NH$_2$
N-(1-Naphthoyl)-HisTrpAlaValD-AlaHisD-ProψPhe-NH$_2$
N-(((3',4',5'-Trimethoxy)-3-Phenyl)Propionyl)-HisTrpAlaValD-AlaHisD-ProψPhe-NH$_2$
N-((6'-Methoxy)-2-(2-Naphthoyl)Propionyl)-HisTrpAlaValD-AlaHisD-ProψPhe-NH$_2$
N-(((3'-Trifluoromethyl)-3-Phenyl)Propionyl)-HisTrpAlaValD-AlaHisD-ProψPhe-NH$_2$
N-(((S)-3-Phenyl)Butyryl)-HisTrpAlaValD-AlaHisD-ProψPhe-NH$_2$
N-(((4'-Methoxy)-3-Phenyl)Propionyl)-HisTrpAlaValD-AlaHisD-ProψPhe-NH$_2$
N-((((S)-2-Hydroxy)-2-Phenyl)Acetyl)-HisTrpAlaValD-AlaHisD-ProψPhe-NH$_2$
N-((3-Phenyl)Propionyl)-HisTrpAlaValD-AlaHisProψPhe-NH$_2$ N-((2-Methyl-2-Phenyl)Propionyl)-HisTrpAlaValD-AlaHis
  D-ProψPhe-NH$_2$
N-(3-(1-Naphthyl)Propionyl)-HisTrpAlaValD-AlaHis
  D-ProψPhe-NH$_2$
N-(((R)-3-Phenyl)Butyryl)-HisTrpAlaValD-AlaHis
  D-ProψPhe-NH$_2$
N-((9-Fluoroenoyl)1-Carbonyl)-HisTrpAlaValD-AlaHis
  D-ProψPhe-NH$_2$
N-(((2'-Methoxy)-3-Phenyl)Propionyl)-HisTrpAlaVal
  D-AlaHisD-ProψPhe-NH$_2$
N-(((2',5'-Dimethoxy)-3-Phenyl)Propionyl)-HisTrpAlaVal
  D-AlaHisD-ProψPhe-NH$_2$
N-((3-Phenyl)Propionyl)-HisTrpAlaValD-AlaHis
  D-ProψTyr-NH$_2$
N-(((2',3'-Dimethoxy)-3-Phenyl)Propionyl)-HisTrpAlaVal
  D-AlaHisD-ProψPhe-NH$_2$
N-((3-Phenyl)Propionyl)-HisTrpAlaVal
  D-AlaHis(3-(2-Pyrrolidinyl-3-Hydroxy)Propionyl)-Phe-NH$_2$
((Isoquinolylcarbonyl)-HisTrpAlaValD-AlaHis
  D-ProψPhe-NH$_2$
N-((3-Phenyl)Propionyl)-HisTrpAlaValD-AlaHis
  D-ProψPhe-NH$_2$ Pharmaceutically acceptable salts or pro-drugs of polypeptides of the formula (I) are also included within the scope of the present invention. Suitable pharmaceutically acceptable salts are acid addition salts when the polypeptide is sufficiently basic e.g., contains one or more basic residues such as histidine.

A suitable pharmaceutically-acceptable acid-addition salt of the invention may be formed with an inorganic acid, for example hydrochloric acid, hydrobromic acid, sulphuric acid or phosphoric acid, or with an organic acid, for example acetic acid, citric acid, maleic acid, fumaric acid, succinic acid, tartaric acid or trifluoroacetic acid.

The invention provides, as a further feature, any one or more of the preferred compounds together with their pharmaceutically acceptable acid-addition salts.

The polypeptides of the invention may be prepared by any process well known in the art of peptide chemistry to be applicable to the synthesis of analogous compounds. Thus, for example, a polypeptide of the invention may be obtained by procedures analogous to those disclosed in "Solid Phase Peptide Synthesis" by Stewart and Young (published by the Pierce Chemical Company, Illinois, 1984), "Principles of Peptide Synthesis" (published by Springer-Verlag, Berlin, 1984), "Practice of Peptide Synthesis" (published by Springer-Verlag, Berlin, (1984), and "The Synthesis of a Tetrapeptide (J.Am.Chem.Soc., 83 2149(1963)).

Preferred processes for the manufacture of a polypeptide of the invention include, for example:
(a) the removal of one or more conventional peptide protecting groups from a protected polypeptide to give a polypeptide of the invention of formula I;
(b) the formation of an amide bond by coupling two peptide units, one containing a carboxylic acid group, or a reactive derivative thereof, and the other containing an amino group, such that a protected or unprotected polypeptide having the sequence indicated in formula I is produced whereafter, if necessary, the protecting groups are removed using process (a) above.

In process (a) there may be as many protecting groups in the starting material as there are radicals which may require protection, for example some or all of those groups which exist in the product as free hydroxy groups or basic amino groups (whether primary or secondary amino groups). The protecting group or groups may be chosen from those described in the standard text books on peptide chemistry stated above. Various methods for the removal of the protecting group or groups are also described in those books.

In process (a) a suitable protecting group for a basic amino group (whether at the N-terminus or in an amino acid side chain) is, for example, an arylmethoxycarbonyl group, which may be removed by hydrogenation over a catalyst, for example palladium-on-charcoal or it may be removed by treatment with an inorganic acid, for example anhydrous hydrogen fluoride or hydrogen bromide.

In process (a) a particularly suitable protecting group for a basic amino group is, for example, an alkoxycarbonyl group, for example a Boc-group, which may be removed by treatment with an organic acid, for example trifluoroacetic acid, or it may be removed by treatment with an inorganic acid, for example anhydrous hydrogen chloride or hydrogen bromide; or for example a 9-fluorenylmethoxycarbonyl group, which may be removed by treatment with an organic base, for example piperidine.

In process (a) a particularly suitable protecting group for the basic amino group in the side chain of Histidine is, for example, an arylsulphonyl group, for example a tosyl group, which may be removed by treatment with hydroxylamine, for example an N-hydroxytriazole, particularly 1-hydroxybenzotriazole, benzyloxymethyl or t-butyloxymethyl.

In process (a) a suitable protecting group for a hydroxy group is, for example, an arylmethyl group, for example a benzyl group, which may be removed by treatment with an inorganic acid, for example anhydrous hydrogen fluoride, or it may be removed by hydrogenation over a catalyst, for example palladium-on-charcoal; or it may be for example, an esterifying group, for example an acetyl or benzoyl group, which may be removed by hydrolysis with a base, for example sodium hydroxide.

In process (a) a suitable protecting group for a carboxy group is, for example, an esterifying group, for example an arylmethyl group, for example a benzyl group, which may be removed by treatment with an inorganic acid, for example anhydrous hydrogen fluoride, or it may be removed by hydrogenation over a catalyst, for example palladium-on-charcoal; or, an alkyl group, $C_{1-6}$ alkyl, for example a tert-butyl group which may be removed by treatment with an organic acid, for example trifluoroacetic acid.

In process (a) particularly suitable protection for a carboxy group at the C-terminus is afforded by the formation of, for example, an ester, for example the ester formed by the coupling of the C-terminus amino acid and a resin, for example a hydroxymethylated styrene-divinylbenzene crosslinked resin; or by the formation of, for example, an amide, for example the amide formed by the coupling of the C-terminus amino acid and a resin, for example a methylbenzhydrylamine styrene-divinylbenzene crosslinked resin.

In process (b) any one of the standard peptide coupling reactions may be used, for example those described in the standard text books on peptide chemistry stated above.

In process (b) it is to be understood that a peptide unit may contain just one protected or unprotected amino acid.

In process (b) a suitable coupling reaction is, for example, a solution-phase coupling reaction, for example an active ester coupling, an azide coupling or a coupling involving N,N'-dicyclohexylcarbodiimide, 1-hydroxybenzotriazole and BOP(Benzotriazole-1-yl-oxy-tris-(dimethylamino)-phosphonium hexafluorophosphate.

In process (b) a suitable reactive derivative of the peptide unit containing a carboxylic acid group is, for example, an acyl halide, for example an acyl chloride formed by the reaction of the acid and an inorganic acid chloride, for example thionyl chloride; a mixed anhydride, for example an anhydride formed by the reaction of the acid and a haloformate, for example isobutyl chloroformate; or an acyl azide, for example an azide formed by the reaction of the acid and an azide such as diphenylphosphoryl azide.

In process (b) a particularly suitable reactive derivative of the peptide unit containing a carboxylic acid group is, for example, the product of the reaction of the acid and a carbodiimide, for example N,N'dicyclohexylcarbodiimide or N,N'-diisopropylcarbodiimide, or it is the product of the reaction of the acid, an N-hydroxytriazole, for example 1-hydroxybenzotriazole, and a carbodiimide, for example N,N'-dicyclohexylcarbodiimide or N,N'-diisopropylcarbodiimide.

In process (b) a preferred strategy is, for example, to use a solid-phase synthesis wherein the amino acid which is to become the C-terminus amino acid of a polypeptide of the invention is protected at the alpha amino group and, if necessary, in the side-chain and coupled to a solid support, for example a resin, for example a hydroxymethylated or a methylbenzhdrylamine styrene-divinylbenzine crosslinked resin via an ester or amide linkage respectively, whereafter the protecting group on the alpha-amino group is removed. The amino acid which is to be attached to the C-terminus amino acid is protected at the alpha-amino group and, if necessary, in the side-chain and coupled to the C-terminus amino acid which remains attached to the solid support. The step-wise process of deprotection of the alpha-amino group and coupling to the next amino acid is repeated to give a protected or unprotected polypeptide attached to the solid support.

The protected or unprotected polypeptide may be released from the hydroxymethylated resin solid support, for example, hydrolysis, for example acid hydrolysis, with, for example, an organic acid, for example trifluoroacetic acid or with, for example, an inorganic acid, for example anhydrous hydrogen fluoride or hydrogen bromide; or the polypeptide is released by, for example, alcoholysis, for example methanolysis, in the presence of a base, for example an organic base, for example diisopropylethylamine whereafter, if necessary, the protecting groups are removed using process (a) above.

When a methylbenzhydrylamine resin is used, the protected or unprotected polypeptide may be released from the solid support, for example by treatment with an inorganic acid, for example hydrogen fluoride, whereafter, if necessary the protecting groups are removed using process (a) above.

In process (b) a further preferred strategy is, for example, to use a solid-phase synthesis wherein an amino acid which is to become a link within the chain of amino acids forming a polypeptide of the invention is protected at the alpha-amino group and, if necessary, in the side-chain and coupled to a solid support, for example a resin as described above, whereafter the protecting group on the alpha-amino group is removed. The amino acid which is to be attached to the amino acid which has been coupled to the solid support is protected at the alpha-amino group and, if necessary, in the side-chain and coupled to the amino acid which remains coupled to the solid support. The step-wise process of deprotection of the alpha-amino group and coupling to the next amino acid is repeated to give a protected or unprotected polypeptide attached to the solid support.

The protected or unprotected polypeptide may be released from the solid support, for example, using one of the methods described above whereafter a further peptide unit can be coupled using a solution-phase coupling reaction as described for process (b) above, and whereafter, if necessary, the protecting groups are removed using process (a) above.

The polypeptides of the present invention have a bombesin antagonist effect, which may be demonstrated by their ability to inhibit Bombesin C stimulated mitogenesis of mouse Swiss 3T3 fibroblast cells as determined by the uptake of [$^3$H]-thymidine.

According to a further feature of the invention there is provided a pharmaceutical composition which comprises a polypeptide of formula I, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example, a snuff, nasal spray or nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients. However, in the case of a composition for oral administration, it may be convenient for the composition to include a coating to protect the polypeptide active ingredient from the actions of enzymes in the stomach.

A composition of the invention may also contain, in addition to the polypeptide of the invention, one or more known antitumour substances selected from, for example, mitotic inhibitors, for example vinblastine; alkylating agents, for example cis-platin, carboplatin and cyclophosphamide; antimetabolites, for example 5-fluorouracil, cytosine arabinoside and hydroxyuea; intercalating antibiotics, for example adriamycin and bleomycin; enzymes, for example asparaginase, topoisomerase inhibitors, for example etoposide and biological response modifiers, for example interferon.

A preferred composition of the invention is, for example, one suitable for oral administration in unit dosage form, form example a tablet or capsule which contains from 2.5 to 500 mg. and preferably 10 to 100 mg, of polypeptide in each unit dose, or one suitable for parenteral administration which contains from 0.5 to 100 mg of polypeptide per ml, and preferably 1 to 10 mg of polypeptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is, for example, a continuous release formulation, for example a formulation of the type described in U.S. Pat. No. 4,767,628 and U.S. Pat. No. 5,004,602. A preferred slow release parenteral formulation contains from 10 to 100 mg of polypeptide per unit dose. Another preferred slow release formulation is a micro-encapsulated polypeptide using a biodegradable biocompatible copolymer.

These preparations are preferably administered intravenously, although administration may also be effected by means of subcutaneous, intramuscular, or intradermal injection.

Polypeptides are therapeutic agents requiring specialized pharmaceutical formulations for effective, safe and convenient use by patients. Since even small oligopeptides like thyrotrophin releasing hormone (TRH) have very low oral activity, and larger molecules are inactivated by endopeptidases in the gastrointestinal tract, long-term treatment requires daily injection or administration from small portable infusion pumps. On the other hand, there are a number of potential approaches to self-administered methods, (e.g. nasal application, suppositories), or to controlled-release formulations such as injectable microcapsule suspensions and implants.

Medicaments suitable for transdermal administration may take the form of an optionally buffered aqueous solution of a compound of formula (I) and may be delivered by passive diffusion or by electrically-assisted transport, for example, iontophoresis (see, for example, Pharmaceutical Research 3(6), 318 (1986)).

The composition of the invention will normally be administered such that a daily oral dose will be from 0.1 mg/kg, to 50 mg/kg, and most preferably from 0.1 mg/kg to 25 mg/kg and a daily parenteral dose, will be from 20 micrograms/kg to 10 mg/kg more preferably from 100 micrograms to 10 mg/kg.

According to a further feature of the invention there is provided a method for producing a bombesin antagonist effect in a warm-blooded animal, such as man, in need of such treatment which comprises administering to said animal an effective amount of a polypeptide of formula I or a pharmaceutically-acceptable salt thereof. The invention also provides the use of such a polypeptide of formula I or a pharmaceutically-acceptable salt thereof in the production of a new medicament for use in the treatment of a disease or medical condition mediated by bombesin or a bombesin-like peptide.

The compounds of the present invention are useful for inhibiting the binding of gastrin releasing peptide in cells. The compounds of the present invention also inhibit the growth of cancer cells.

A polypeptide of the invention is useful in the treatment of malignant disease, for example malignant disease in the lung, such as human small cell lung cancer, for example, malignant disease in the pituitary gland, adrenal gland, pancreas or within the skin. In particular, a polypeptide of this invention is useful for the symptomatic relief and/or treatment of exocrine pancreatic adenocarcinoma. A polypeptide of the invention is useful in the treatment of conditions associated with the over-production of bombesin or bombesin-like peptides (such as gastrin releasing factor), for example the over-production of gastrin in the gut. The production of gastrin in animals has been linked to the suppression of the release of growth hormone and prolactin. The polypeptides of the invention may therefore be used to promote the availability of growth hormone in man or animals in need of such treatment. The polypeptides of the invention may also be used in the treatment of conditions associated with the failure of normal physiological control of the regulation of gastric acid secretion.

According to further aspects of the invention, there are provided:
(a) polypeptides of the invention for use in therapy;
(b) pharmaceutical formulations containing polypeptides of the invention, at least one pharmaceutical carrier or excipient and, optionally, one or more other therapeutic ingredients;
(c) the use of polypeptides of the invention in the manufacture of a medicament for the treatment of cancer;
(d) the use of a polypeptide of the invention in the manufacture of a medicament for the treatment of:
  (i) Entercutaneous Fistula
  (ii) Type II diabetes, type I diabetes
  (iii) Zollinger-Ellison Syndrome
  (iv) Pancreatic islet carcinoma
  (v) Acromegaly
  (vi) Psoriasis e.g. Chronic Plaque Psoriasis
  (vii) Postoperative Small Bowel Fistula
  (viii) Dumping Syndrome
  (ix) Malignant Insulinoma
  (x) Pituitary Growth Hormone Cell Adenoma
  (xi) Thyrotropin-Secreting Pituitary Adenomas
  (xii) Small Cell Lung Cancer
(e) a method for inhibiting the growth of cells that are sensitive to the growth promoting activity of gastrin releasing peptide in a mammal (such as a human) in need of such treatment which comprises the administration to said mammal of a growth inhibiting amount of a polypeptide of the invention to said mammal.

The following examples serve to illustrate the preparation of polypeptides of the present invention and their biological properties:

EXPERIMENTAL SECTION

Materials

The following abbreviations are used throughout
BOC=tertiary butyloxycarbonyl
TLC=Thin layer Chromatography
NMR=Nuclear Magnetic Resonance
MS=Mass Spectrometry The following items were obtained from Advanced Chemtech, Inc., P.O. Box 1403, Louisville, Ky. 40201 U.S.A.: p-Methylbenzhydrylamine resin.HCl (substitution ranges from 0.56–0.94 meq/g), Trifluoroacetic acid, N-Boc-D-Alanine, N-Boc-L-Alanine, N-Boc-N-Tosyl-Arginine, N-Boc-Glycine, N-Boc-L-Leucine, N-Boc-L-Leucinol, N-Boc-L-Norleucine, N-Boc-D-Phenylalanine, N-Boc-L-Phenylalanine, N-Boc-D-Proline, N-Boc-L-Proline, N-Boc-D-Prolinol, N-Boc-Sarcosine, N-Boc-L-Tryptophan, and N-Boc-L-Valine.

N-Boc-L-im-CBZ-L-Histidine, N-Boc-β-Thienyl-L-Alanine, and 3-(2-Naphthyl)-D-Alanine were acquired from Bachem, Inc., 3132 Kashiwa Street, Torrance, Calif. 90505, U.S.A.

L-Methoxinine (O-Methyl-L-Homoserine) was obtained from Biohellas S.A., 10.Parnithos Street, 154 52 P. Phsychiko, Athens-Greece.

Leucine methyl ester hydrochloride, (+)-6-Methoxy-α-methyl-2-Naphthaleneacetic acid and (S)-6-Methoxyα-methyl-2-Naphthaleneacetic acid were supplied from the Sigma Chemical Company, P.O. Box 14508, St. Louis, Mo. 63178, U.S.A.

Di-tert-butyl Dicarbonate, 4-Fluorophenylalanine, 3-(4-Hydroxyphenyl)propionic acid N-hydroxysuccinimide ester, and both (R) and (S)-3-Phenylbutyric acid were obtained from Fluka Chemical Corp. 980 South Street, Ronkonkoma, N.Y. 11779, U.S.A.

The following were acquired from Aldrich Chemical Co., Inc., 1001 West Saint Paul Avenue, Milwaukee, Wis. 53233, U.S.A.: 3-Phenylpropionic acid (Hydrocinnamic acid), (R) and (S)-3,3,3-Trifluoro-2-Methoxy-2-Phenylpropionic acid, Dicyclohexyamine, 1-Cyclopentanecarboxylic acid, 4-Methylmorpholine, 1-Methylimidazole, Sodium cyanoborohydride and Diisopropylethylamine.

Dichloromethane ($CH_2Cl_2$), N,N-Dimethylformamide (DMF), and N-Methylpyrrolidone were utilized as solvents for solid phase peptide synthesis and were obtained from Baxter Healthcare Corp., Burdick & Jackson Division, Muskegon, Mich. 49442, U.S.A.

The BOP coupling reagent, Benzotriazol-1-yl-oxy-tris-(dimethylamino)phosphonium hexafluorophosphate, was obtained from Richelieu Biotechnologies, Inc., 5726 Laurier Blvd., St-Hyacinthe, QC., J2S 3V8 Canada.

Hydrofluoric acid was acquired from Matheson Gas Products, P.O. Box 85, 932 Paterson Plank Road, East Rutherford, N.J. 07073, U.S.A.

Preparation of Peptides of the Present Invention

Step I. Preparation of Boc-amino Acids

Amino acids that were obtained without the tert-butyloxycarbonyl protecting moiety on the amino group (L-Methoxinine, 4-Fluorophenylalanine) were protected as described below. One equivalent of amino acid was dissolved in 5% aqueous $Na_2CO_3$/1,4-dioxane and cooled to 0° C. Two equivalents of Di-tert-butyl Dicarbonate, in 1,4-dioxane, was added dropwise to the cold amino acid mixture. Upon complete addition, the mixture was allowed to warm to 25° C. and stirred for 12 hours. After reaction had gone to completion, as monitored by TLC, the dioxane was evaporated. The aqueous mixture was acidified with 1N HCl until pH=2, whereupon crystals formed, in most cases, at 60% yield. The solid was filtered and characterized by TLC, NMR, and MS as generally pure enough to continue without further purification. In those extreme cases, such as L-Methoxinine, in which the product that dropped out of the acidic, aqueous solution was a liquid, the product was removed from the aqueous solution with ethyl acetate. The organics were then dried with anhydrous sodium sulphate and the ethyl acetate was evaporated. The liquid residue was dissolved in a small portion of ethyl acetate.

One equivalent of dicyclohexylamine was added to the mixture, which was then diluted with a large excess of diethyl ether. Upon cooling, the Boc-amino acid-dicyclohexylamine salt crystallized out. The solid was filtered (20–30% yield), characterised (TLC, NMR, MS), and was used without further purification.

Step II Preparation of Boc-D-Prolinal

The following procedure is a variation of the reaction performed by Mancuso, et al. In J. Org. Chem. 43, 2481 (1978).

Into a 500 ml three-neck flask, 25 ml of a 2.0M solution of oxalyl chloride in methylene chloride (50 mmoles, solution obtained from Aldrich) was dissolved in 60 mL of dry $CH_2Cl_2$, at −60° C., under $N_2$. Dimethyl sulfoxide (10 ml, 140 mmoles, Aldrich) was dissolved in 25 ml dry $CH_2Cl_2$, and added dropwise to the −60° C. solution, by an addition funnel. This mixture was then stirred for 15 minutes after complete addition. Boc-D-prolinol (10 g, 50 mmoles, Advanced Chemtech) was dissolved in 60 ml dry $CH_2Cl_2$ and chilled to −60° C. in a 500 mL round-bottomed flask, under $N_2$. To facilitate combination of the contents of both cold flasks, the $N_2$ line was set up in series to accommodate both flasks. The oxalyl chloride/DMSO mixture was gradually added to the alcohol solution by $N_2$-pressurized transfer through a double-tipped needle. By manually controlling the $N_2$ flow rate, the contents were transferred from one flask to the other, very slowly, but not dropwise. Upon complete addition, this mixture was stirred for 20 minutes. Lastly, 20 ml of triethylamine (140 mmoles, Kodak) was added slowly, while at −60° C. The mixture was then allowed to warm to room temperature.

The mixture was washed with 50 ml of water. This aqueous layer was then extracted three times with 70 ml of $CH_2Cl_2$. The organics were successively washed with 50 mL each of 5% $NaHCO_3$, 1N HCl, and water. The aqueous washings were extracted with 50 ml of $CH_2Cl_2$, which was then combined with the other organics. After drying the organics with anhydrous sodium sulfate, the solvent was removed by rotary evaporation, The residue was dried on a vacuum pump for 3 hours.

According to NMR, the characteristic —OH peak for Boc-D-prolinol (δ 4.5 ppm) was no longer visible. A sharp singlet at δ 9.4 ppm denoted the presence of the aldehydic proton of Boc-D-prolinal. TLC indicated a product mixture containing no substanial side products, so this was used without further purification.

Step III Preparation of Boc-DProψ(CH$_2$NH)X-MBHA Resin i) Advanced Chemtech's p-methylbenzhydrylamine resin .HCl (p-MBHA) was utilized. Resin substitution ranged from 0.90–0.97 meq/g.

Ten grams of p-MBHA resin (9.0–9.7 mmoles) were placed in a manual peptide shaker (Milligen). The resin was washed twice (3 and 5 minutes) with 10% N,N-diisopropylethylamine (DIEA, Aldrich) in $CH_2Cl_2$, while shaking. The resin was next rinsed twice with $CH_2Cl_2$. Neutralization of the HCl on the resin was indicated by a Kaiser ninhydrin test observed as a very deep blue colour.

The resin was next treated with two equivalents each of Boc-norleucine (Bachem, Torrance, Calif.), benzotriazol-1-yloxy-tris(dimethylamino) phosphonium hexafluorophosphate (BOP, Richelieu Biotechnologies of Canada), and 4-methylmorpholine (Aldrich); all dissolved in 50 ml of N,N-dimethylformamide (DMF). This mixture was shaken for 1 hour and then rinsed twice with $CH_2Cl_2$. Coupling was verified by a Kaiser test (colourless), compared to the previous Kaiser result (blue).

Deprotection of the Boc-group on norleucine was undertaken by shaking the resin in the presence of 50% trifluoroacetic acid (TFA, Advanced Chemtech) in $CH_2Cl_2$ twice, for 5 and 20 minutes. After rinsing the resin once with $CH_2Cl_2$, the excess TFA was neutralized with 10% DIEA/$CH_2Cl_2$ solution for 3 and 5 minutes, with shaking. Following two $CH_2Cl_2$ rinses, the resin was again qualitatively tested with ninhydrin (very deep blue).

The resin was next shaken for 2 hours with 2 equivalents of Boc-D-prolinal in 50 ml of 2% glacial acetic acid in DMF. Over the entire 2 hours, three equivalents of sodium cyanoborohydride (Aldrich) were added slowly and gradually. After rinsing twice with $CH_2Cl_2$, coupling was checked with ninhydrin (colourless). The resin was now ready for standard solid phase peptide synthesis.

Alternative Preparation of Boc-D-Proψ(CH$_2$NH)X-MBHA Resin ii) The following procedures may be used to prepare any D-Proψ(CH$_2$NH)X-MBHA resin, where X=any amino acid with a primary amino group.

A. Boc-D-Proψ(CH$_2$NH)X—OH may be synthesized by the procedures of Martinez, et al., In J. Med. Chem., 28, 1874 (1985), or D. Tourwe, et al., in Peptides 1988: Proceedings of the 20th European Peptide Symposium., Ed. Jung, Bayer; Walter de Gruyter, p. 562–4.

B. This resin may be prepared by coupling Boc-D-Proψ(CH$_2$NH)X—OH to MBHA resin by shaking with BOP and 4-Methylmorpholine (or 1-Methylimidazole) in N-Methyl-pyrrolidone for 2 hours.

Preparation of Intermediates

Preparation of Ethyl 3-(1-(Tert-Butoxycarbonyl)-2-Pyrrolidinyl)-3-Hydroxypropionate Freshly activated zinc powder (0.79 g, 12 mmol, Aldrich) and benzene (50 mL) were placed into a 250-mL two neck round bottom flask under $N_2$. This flask was attached to a Dean-Stark apparatus and 25 mL of benzene was distilled into the trap. Under reflux, a solution of Boc-D-Prolinal (1.90 g, 9.5 mmol) and ethylbromoacetate (2.0 g, 12 mmol, Aldrich) was added dropwise. A crystal of iodine was added to initiate the reaction after half of the dropping solution was added. After complete addition, the mixture was refluxed for 3 hours, cooled, and carefully washed with 0.5 n HCl. The aqueous solution was extracted with ether (25 mL) and the combined organic solution was washed successively with water (30 mL) and saturated $NaHCO_3$ (30 mL), then dried with anhydrous $Na_2SO_4$ and concentrated under vacuum. A yellow oil was chromatographed on silica (with hexane/ethyl acetate) to isolate a colourless oil (1.12 g, 41%).

Mass spectral analysis yielded results at 288(m+1, 20%), 232 (m–tBu+1, 40%), and 188(m–$CO_2Bu$+1, 100%). $^1$H-NMR ($CDCl_3$): δ 4.15 (br m, 3H); 3.92(m, 1H); 3.48(M, 1H); 3.26(m, 1H); 2.40(m, 2H); 1.65–200(br m, 4H); 1.45(s, 9H); 1.25(t, 3H).

Preparation of 3-(1-(Tert-Butoxycarbonyl)-2-Pyrrolidinyl)-3-Hydroxypropionic acid A mixture of ethyl 3-(1-(tert-butoxycarbonyl)-2-pyrrolidinyl)-3-hydroxypropionate (3.06 g, 10.6 mmol) and NaOH (0.80 g, 20 mmol) in $H_2O$:THF:methanol (3:3:1, 35 mL) was stirred at 25° C. for 2 hours. The mixture was concentrated gently (30° C.) under vacuum. The aqueous solution was acidified with 1.0N HCl tp pH=5, and was extracted with ethyl acetate. The organic washings were dried with $MgSO_4$, filtered and vacuum concentrated. This residue was recrystallized from hexane/ethyl acetate resulting in 1.19 g (47%) of a colourless solid (A, mp=122°–4° C.). The mother liquor was concentrated down to a viscous, pale yellow oil (B).

Mass spectral analysis yielded: 260(m+1, 60%); 204(m–tBu+1, 100%), 160(m–100+1, 70%). $^1$H NMR (DMSO): δ 4.09(m, 1H); 3.57(br s, 1H); 3.31(m, 1H); 3.15(m, 1H): 2.10–2.40(m, 2H); 1.60–2.00(m, 4H): 1.38(s, 9H). Elemental analysis: theory, 55.58% C, 8.16% H, 5.40% N; Found, 55.39% C, 8.23% H, 5.37% N. HPLC: one major peak on NOVA PAK $C_{18}$ with 50% methanol/$H_2O$/0.1% TFA/0.1% triethylamine (A=93:7 ratio, B=1:2 ratio observed on extended HPLC). The two products were determined to be different stereoisomers, at the hydroxy position. Both stereoisors were used in individual peptides; the more active of the two is N-((3-Phenyl)Propionyl)-HisTrpAlaVal D-AlaHis(3-(2-Pyrrolidinyl-3-Hydroxy)Propionyl)-Phe-$NH_2$.

Step IV Peptide Synthesis and Purification

The peptides were synthesized using an improved version of the solid phase method described by R. B. Merrifield, "Solid Phase Peptide Synthesis I. The Synthesis of a Tetrapeptide", J. Am. Chem. Soc., 83, 2149(1963), using an Applied Biosystems Model 430A peptide synthesizer.

For the synthesis of "pseudopeptides", the appropriate resin, e.g. Boc-D-Proψ($CH_2NH$)Phe-MBH was loaded in the synthesizer and a standard deprotection (TFA/$CH_2Cl_2$)-neutralization (diisopropylethiamine/$CH_2Cl_2$) program, as supplied by Applied Biosystems (850 Lincoln Centre Drive, Foster City, Calif. 94404 U.S.A.) was used.

Boc-protected amino acids were coupled to the resin using a modified program to suit the BOP coupling procedure, as described by Dung Le-Nguyen, Annie Heik, and Bertrand Castro, J. Chem. Soc., Perkins Trans. 1, 1915(1987). The coupling protocol involved dissolving 1 mMole of Boc-protected amino acid, 1 mMole BOP, and 1 ml of 1M 1-Methylimidazole in 7 ml of DMF. The mixture was added to 0.5 mMoles of resin, mixed for 1 hour, and filtered. Afterwards, a series of DMF and $CH_2Cl_2$ washes are performed.

After the peptide was assembled on the resin, it was deblocked and cleaved from the resin with liquid HF containing 10% anisole, in a variation of the method described by S. Sakakibara, et al., in Bull. Chem Soc. Jap., 40, 2164(1967). The peptide and resin were next washed with ethyl acetate and then the peptide was extracted from the resin with an aqueous 1% acetic acid solution. The peptide solution was then lyophilized to obtain the dry, solid peptide.

The peptides were then purified by reverse-phase liquid chromatography using a Vydac 218TP1022 column on a Waters Delta Prep 3000 system equipped with a Gilson Model 116 ultraviolet detector. Purification was achieved by equilibrating the column with 0.1% TFA in water and developing with a linear gradient of acetonitrile from 1–40% in 20 minutes at a flow rate of 20 mL/min. Samples were collected manually and checked for purity on a Spectra-Physics analytical HPLC system (including SP8700, SP8440, SP8780, and SP4200) utilizing a Vydac 218TP54 column. A flow rate of 1.5 mL/min. was employed using a 0.1% TFA/acetonitrile gradient from 10–60% ACN in 10 minutes.

SYNTHESIS OF N-((3-Phenyl)Propionyl)HisTrpAlaValDAlaHis DPro-psi($CH_2NH$)Phe-$NH_2$ Methylbenzhydrylamine (MBHA) resin (5.0 g., 4.7 mmoles, Advanced Chemtech) was washed twice (3 & 5 min.) with 10% diisopropylethylamine (DIEA, Aldrich) in dichloromethane (DCM) on a Milligen Peptide Shaker. The resin was then washed with DCM and N,N-dimethylformamide (DMF). A solution containing 2.5 g of Boc-Phe (9.4 mmol., Chemtech), 4.3 g of BOP Reagent (9.4 mmol., Richlieu Biotechnologies), and 0.95 mL of 4-Methylmorpholine (8.6 mmol., Aldrich) were shaken on the resin for 1 h. The resin was then washed successively with methanol and DCM and coupling was verified via a Kaiser Ninhydrin qualitative test.

A portion of the Boc-Phe-MBHA (3.06 g., 2.8 mmol) was deprotected by treating with 50% trifluoro-acetic acid (TFA, Chemtech) in DCM for 5 and 20 min. periods. The resin was washed twice with DCM. The acid was then neutralized by shaking for 3 and 5 min. with 10% DIEA solution and washed with DCM and DMF. The $H_2N$-Phe-MBHA was shaken in a 1% acetic acid/N-methylpyrrolidone solution containing 1.2 g of Boc-DProlinal (6.0 mmol., synthesis described previously) over 2 h. Sodium cyanoborohydride (0.54 g., 8.62 mmol., Aldrich) was added in four portions during the 2 h. (approximately every 20 min.) The resin was washed with methanol and DCM and tested with ninhydrin. Alternatively the same resin can be prepared as described in the alternative preparation above.

The subsequent amino acids (Boc-His(Z), Boc-P-Ala, Boc-Val, Boc-Ala, Boc-Trp, Boc-His(Z) and 3-Phenylpropionic acid) were added to the sequence by an Applied Biosystems Automated Peptide Synthesizer (Model 430A) via the same procedure described for coupling, deprotection and neutralization involving Boc-Phe (utilizing 0.5 mmol. of resin and 1 mmol. each of amino acid, BOP, and 4-Methylmorpholine). All amino acid couplings performed by the 430A were checked by qualitative Kaiser tests on resin samples provided by the instrument after the completion of each coupling.

The peptide (approximately 1.0 g.) was cleaved from the MBHA resin by treating the peptide-resin with hydrogen fluoride (approximately 10 mL) at 0° C. for 1 h. The peptide was precipitated and filtered with the MBHA resin by ethyl acetate. The peptide was then extracted from the resin using 1% aqueous acetic acid and isolated upon freeze-drying this extract.

A portion of the peptide (100 mg) was purified on a Vydac C-18 preparative column (Chemtech) utilizing a 0.1% TFA/$H_2O$:0.1% TFA/acetonitrile gradient. The collected fractions were verified by an analytical Vydao C-18 column (Chemtech), and those samples reflecting pure peptide were combined and freeze-dried. Approximately 15 mg of peptide was isolated. After characterization by FAB-Mass Spectrum ($MH^+$=1081.7) and Amino Acid Analysis [Ala(2.19), His(1.68), Val(1.12)], 12.2 mg remained (12% yield based on HPLC).

Analytical Methods

Purity was monitored by analytical HPLC using a Spectra-Physics analytical HPLC system, including SP8700, SP8440, SP8780, and SP4200.

A Vydac 218TP54 column was utilized with a flow rate of 1.5 mL/min. of 1 0.1% TFA/acetonitrile gradient.

The correct composition of each peptide was assessed by Amino Acid Analysis and (FAB) Mass Spectroscopy. Amino Acid Analysis was performed by the following procedure. Approximately 1–10 nanomoles of peptide were placed into an acid washed Pyrex test tube. The peptide was hydrolyzed under reduced $N_2$ atmosphere with 6N HCl with 1% phenol for 1 hour at 150° C. The peptide was then dried with a 2:2:1 mixture of ethanol:water:triethylamine, and derivatized with a 7:1:1:1 solution of ethanol:water:triethylamine:phenyliosothiocyanate. The derivatized amino acids then analyzed by reverse-phase chromatography.

Fast atom bombardment (FAB) mass spectra were obtained on a VG 70SQ mass spectrometer of EBQQ geometry using a VG 11-250J Data System for data acquisition. The mass spectrometer was operated at seven kilovolts accelerating potential and a resolution of 1000 (10% valley definition). The FAB gun used in the experiments was Ion Tech FAB11N operating at seven kilovolts potential and one milliamperes current. Xenon was used as the bombardment gas at a pressure of $1\times10^{-5}$ millibars source pressure. The sample of interest was dissolved in glycerol prior to analysis by FAB-MS.

Biological Results

The peptides were evaluated in their activity to inhibit GRP binding to Swiss 3T3 cells. Antagonistic activity was measured by inhibition of the mitogenic stimulation of quiescent 3T3 ROZ cells. 3T3 ROZ cells were obtained from Enrique Rozengurt, Imperial Cancer Research Fund, P.O. Box 123, Lincoln's Inn Fields, London WC2A 3PX, England. Cells were incubated for eighteen hours with 10 ng/mL of BN either alone or in the presence of an antagonist. Cells were then pulsed-labeled for 2 hours with $^3$H-thymidine and washed. The incorporated $^3$H was then counted.

Bombesin exposure resulted in increased cpm over media control up to a maximum response. Potency of antagonists was measured by inhibition of this maximum response down to baseline level. $IC_{50}$ values were determined from titration curves. Analogues and available $IC_{50}$ values are listed in Table I.

TABLE 1

| STRUCTURE | $IC_{50}$(M) | $MH^+$(FAB)-MS | AAA |
|---|---|---|---|
| N—((R)-2-(6-Methoxy-2-Naphthyl)Propionyl)—HisTrpAlaValD—Ala HisD—ProΨNle—NH$_2$ | $3 \times 10^{-10}$ | 1128 | Ala(1.85), His(1.79), Val(1.00) |
| N—((S)-2-(6-Methoxy-2-Naphthyl)Propionyl)—HisTrpAlaValD—Ala HisD—ProΨNle—NH$_2$ | $1.77 \times 10^{-8}$ | 1128 | Ala(1.97), His(1.81), Val(1.00) |
| N—((S)-3-Phenylbutyryl)—HisTrp AlaValD—AlaHisD—ProΨNle—NH$_2$ | $4.71 \times 10^{-8}$ | 1061.6 | Ala(1.92), His(1.71), Val(1.00) |
| N—((R)-3-Phenylbutyryl)—HisTrp AlaValD—AlaHisD—ProΨNle—NH$_2$ | $7.54 \times 10^{-8}$ | 1061.6 | Ala(1.77), His(1.65), Val(1.00) |
| N—((3-Phenyl)Propionyl)—HisTrp AlaValD—Ala(3-(2-Thienyl)—Ala)D—ProΨNle—NH$_2$ | $2.35 \times 10^{-7}$ | 1063.5 | N/A |
| N—((S)-3,3,3-Trifluoro-2-Methoxy-2-Phenyl-Propionyl)—HisTrpAla ValD—AlaHisD—ProΨNle—NH$_2$ | not yet tested | 1132 | Ala(2.40), His(1.15), Val(1.00) |
| N—((R)-3,3,3-Trifluoro-2-Methoxy-2-Phenyl-Propionyl)—HisTrpAla ValD—AlaHisD—ProΨNle—NH$_2$ | not yet tested | 1131.3 | Ala(1.90), His(1.19), Val(1.00) |
| N—(((4'-Hydroxy-3-Phenyl)Propionyl)—ProD—ArgGlyD—PheHis TrpAlaValGlyHisD—ProΨNle—NH$_2$ | $1.99 \times 10^{-8}$ | | Ala(1.00), Arg(1.05), Gly(2.15), His(1.73), Phe(1.02), Pro(1.10), Val(0.95) |
| N—(((4'Hydroxy)-3-Phenyl)Propionyl)—ProD—ArgGlyD—PheHis TrpAlaValGlyHisProΨNle—NH$_2$ | $7.96 \times 10^{-8}$ | 1508.2 | Ala(0.96), Arg(1.07), Gly(2.08), His(1.78), Phe(1.03), |

TABLE 1-continued

| STRUCTURE | IC$_{50}$(M) | MH$^+$(FAB)-MS | AAA |
|---|---|---|---|
| | | | Pro(1.17), Val(0.91) |
| N—((3-Phenyl)Propionyl)—HisTrp AlaValD—AlaHisD—ProΨMethoxinine-NH$_2$ | 3.43 × 10$^{-8}$ | 1049.4 | Ala(2.09), His(1.84), Val(1.07) |
| N—((3-Phenyl)Propionyl)—HisTrp AlaValD—AlaHisD—ProΨPhe—NH$_2$ | 8.30 × 10$^{-12}$ | 1081.7 | Ala(2.19), His(1.68), Val(1.12) |
| N—((3-Phenyl)Propionyl)—HisTrp AlaValD—AlamisD—ProΨLeu—NH$_2$ | 2.72 × 10$^{-8}$ | 922.0 | Ala(2.02), His(0.75), Val(1.00) |
| N—((3-Phenyl)Propionyl)—HisTrp ProValD—ProHisD—ProΨLeu—NH$_2$ | 6.92 × 10$^{-7}$ | 1099.9 | His(1.73), Pro(2.06), Val(1.00) |
| N—(((3'-Trifluoromethyl)-3-Phenyl) Propionyl)—HisTrpAlaValD—AlaHisD—ProΨLeu—NH$_2$ | 2.70 × 10$^{-9}$ | 1116.0 | Ala(1.92), His(1.57), Val(1.00) |
| N—((3-Phenyl)Propionyl)—(3-(2-Thienyl)—Ala—TrpAlaValD—AlaHisD—ProΨLeu—NH$_2$ | 4.70 × 10$^{-9}$ | 1064.0 | Ala(1.96), His(0.75), Val(1.00) |
| N—((1-Cyclopentyl)carboxyl)—D—ArgD—AlaD—PheHisTrpAlaValGly HisD—ProΨNle—NH$_2$ | 1.75 × 10$^{-8}$ | 1371.6 | Ala(1.93), Arg(1.04), Gly(1.03), His(1.91), Phe(1.04), Val(1.04) |
| N—((3-Phenyl)Propionyl)—HisTrp AlaValGlyHisD—ProΨNle—NH$_2$ | 2.00 × 10$^{-7}$ | 1034.1 | Ala(0.99), Gly(1.11), His(1.94), Val(0.96) |
| N—((1-Cyclopentyl)carboxyl)—D—ArgD—AlaD—PheHisTrpAlaValD—ProΨNle—NH$_2$ | 1.73 × 10$^{-8}$ | 1386.7 | Ala(2.90), Arg(1.07), His(1.93), Phe(1.05), Val(1.05) |
| N—((3-Phenyl)Propionyl)—HisTrp AlaValD—AlaHisD—ProΨNle—NH$_2$ | 3.10 × 10$^{-9}$ | 1048.2 | Ala(2.02), His(1.90), Val(1.08) |
| TyrProD—ArgGlyD—PheHisTrpAla ValGlyHisD—ProΨNle—NH$_2$ | 8.54 × 10$^{-8}$ | 1522.2 | Ala(1.03), Arg(0.97), Gly(2.07), His(2.03), Phe(1.00), Pro(0.93), Tyr(0.87), Val(1.11) |
| D—ArgGlyD—PheHisTrpAlaValGly HisD—ProΨNle—NH$_2$ | 2.00 × 10$^{-7}$ | 1262.5 | Ala(0.97), Arg(1.05), Gly(1.96), His(1.94), Phe(1.04), Val(1.04) |
| N—((3-Phenyl)Propionyl)—HisTrp AlaValD—AlaHis(4-FluoroPhe)—NH$_2$ | 7.87 × 10$^{-8}$ | 1017.0 | Ala(1.87), His(0.86), Val(1.00) |
| N—((3-Phenyl)Propionyl)—HisTrp AlaValD—AlaHisD—ProPhe—NH$_2$ | 3.65 × 10$^{-8}$ | 1096 | Ala(2.13), His(2.31), Phe(1.11), Pro(1.24), Val(1.00) |
| N—((3-Phenyl)Propionyl)—HisTrp AlaValD—AlaHisD—ProΨ(3-(2-Naphthyl)—D—Ala)—NH$_2$ | 2.65 × 10$^{-8}$ | 1132.4 | Ala(1.96), His(1.42), Val(1.00) |
| N—((3-Phenyl)Propionyl)—HisTrp AlaValD—PheHisD—ProΨPhe—NH$_2$ | 4.32 × 10$^{-8}$ | 1157.4 | Ala(1.15), His(1.76), Phe(0.99), Val(1.00) |
| D—PheHisTrpAlaValD—AlaHisD—ProΨPhe—NH$_2$ | <5.47 × 10$^{-10}$ | 1093.2 | Ala(1.98), Phe(0.92), Val(1.00) |
| N—((3-Phenyl)Propionyl)—D—Pro ArgGlyD—PheHisTrpAlaValD—Ala HisD—ProΨPhe—NH$_2$ | <3.90 × 10$^{-10}$ | 1540 | Ala(1.83), Arg(1.02), Gly(0.94), His(1.54), Phe(0.85), Pro(0.94), |

TABLE 1-continued

| STRUCTURE | IC$_{50}$(M) | MH$^+$(FAB)-MS | AAA |
|---|---|---|---|
| N—((3-Phenyl)Propionyl)—3-(2-Thienyl)—Ala)—TrpAlaVal<u>D</u>—Ala His<u>D</u>—ProΨPhe—NH$_2$ | $3.65 \times 10^{-8}$ | | Val(1.00) Ala(1.92), His(0.59), |
| N—((3-Phenyl)Propionyl)—HisTrp AlaVal-Sarcosine)—His<u>D</u>—ProΨPhe—NH$_2$ | $<5.55 \times 10^{-10}$ | | Val(1.00) Ala(1.02), His(2.06), |
| N—(((4'-Hydroxy)-3-Phenyl) Propionyl)—HisTrpAlaVal<u>D</u>—AlaHis<u>D</u>—ProΨPhe—NH$_2$ | $<5.47 \times 10^{-10}$ | 1098 | Val(1.00) Ala(2.04), His(1.96), |
| N—(((2',6'-Dichloro)-2-Phenyl) Acetyl)—HisTrpAlaVal<u>D</u>—AlaHis<u>D</u>—ProΨNle—NH$_2$ | $9.07 \times 10^{-7}$ | 1103 | Val(1.00) Ala(1.85), His(1.83), |
| N(((3',4'-Dichloro)-2-Phenyl) Acetyl)—HisTrpAlaVal<u>D</u>—AlaHis<u>D</u>—ProΨNle—NH$_2$ | $<5.44 \times 10^{-10}$ | 1103.5 | Val(1.00) Ala(2.06), His(1.79), |
| N—(((4'-Hydroxy)-2-Phenyl) Acetyl)—HisTrpAlaVal<u>D</u>—Ala His<u>D</u>—ProΨNle—NH$_2$ | $1.91 \times 10^{-9}$ | 1050.1 | N/A |
| N—(1-Naphthoyl)—HisTrpAlaVal<u>D</u>—AlaHis<u>D</u>—ProΨNle—NH$_2$ | $9.35 \times 10^{-10}$ | 1069.9 | N/A |
| N—((3,7-Dihydroxy)-2-Naphthoyl)—HisTrpAlaVal<u>D</u>—AlaHis<u>D</u>—ProΨNle—NH$_2$ | $2.36 \times 10^{-8}$ | 1101.6 | Ala(1.34), His(2.05), Val(1.00) |
| N—(((2,3-Dihydroxy)-2-Phenyl) Acetyl)—HisTrpAlaVal<u>D</u>—AlaHis<u>D</u>—ProΨNle—NH$_2$ | $1.22 \times 10^{-7}$ | 1065.5 | Ala(2.23), His(1.90), Val(1.00) |
| N—(2-(3-Pyridyl)Acetyl)—HisTrp AlaVal<u>D</u>—AlaHis<u>D</u>—ProΨNle—NH$_2$ | $3.87 \times 10^{-7}$ | 1034.6 | Ala(2.26), His(2.00), Val(1.00) |
| N—(2-(2-Thienyl)Acetyl)—HisTrp AlaVal<u>D</u>—AlaHis<u>D</u>—ProΨNle—NH$_2$ | $2.98 \times 10^{-8}$ | 1040 | Ala(2.15), His(1.63), Val(1.00) |
| N—(((3-Fluoro)-3-Phenyl)Prop-ionyl)—HisTrpAlaVal<u>D</u>—AlaHis<u>D</u>—ProΨNle—NH$_2$ | $3.00 \times 10^{-9}$ | 1066 | Ala(2.14), His(1.66), Val(1.00) |
| N—(((3,4-Dihydroxy)-2-Phenyl) Acetyl)—HisTrpAlaVal<u>D</u>—AlaHis<u>D</u>—ProΨNle—NH$_2$ | $4.63 \times 10^{-8}$ | 1079 | Ala(2.13), His(1.43), Val(1.00) |
| N—(((R)-(−)-2-Phenyl)Propionyl)—HisTrpAlaVal<u>D</u>—AlaHis<u>D</u>—ProΨPhe—NH$_2$ | $9.25 \times 10^{-10}$ | 1081.2 | Ala(2.07), His(1.51), Val(1.00) |
| N—(((S)-(+)-2-Phenyl)Propionyl)—HisTrpAlaVal<u>D</u>—AlaHis<u>D</u>—ProΨPhe—NH$_2$ | $2.77 \times 10^{-9}$ | 1081.1 | Ala(2.05), His(1.44), Val(1.00) |
| N—(((Trans)-2-Phenyl)-Cyclopro-panoyl)—HisTrpAlaVal<u>D</u>—AlaHis<u>D</u>—ProΨPhe—NH$_2$ | $1.46 \times 10^{-9}$ | 1093.1 | Ala(1.99), His(1.44), Val(1.00) |
| N—(3-(10-Phenothiazinyl)Prop-ionyl-HisTrpAlaVal<u>D</u>—AlaHis<u>D</u>—ProΨPhe—NH$_2$ | $2.66 \times 10^{-8}$ | 1202.1 | Ala(2.25), His(1.58), Val(1.00) |
| N—((3-Methyl-3-Phenyl)Butyryl)—HisTrpAlaVal<u>D</u>—AlaHis<u>D</u>—ProΨPhe—NH$_2$ | $1.44 \times 10^{-8}$ | 1109.5 | Ala(2.07), His(1.63), Val(1.00) |
| N—(((2'-Trifluoromethyl)-2-Phenyl)Acetyl)—HisTrpAlaVal<u>D</u>—AlaHis<u>D</u>—ProΨPhe—NH$_2$ | $3.50 \times 10^{-7}$ | 1135.4 | Ala(2.10), His(1.63), Val(1.00) |
| N—(((3'-Trifluoromethyl)-2-Phenyl)Acetyl)—HisTrpAlaVal<u>D</u>—AlaHis<u>D</u>—ProΨPhe—NH$_2$ | $8.81 \times 10^{-8}$ | 1135.4 | Ala(2.10), His(1.60), Val(1.00) |
| N—(((4'-Trifluoromethyl)-2-Phenyl)Acetyl)—HisTrpAlaVal<u>D</u>—AlaHis<u>D</u>—ProΨPhe—NH$_2$ | $1.41 \times 10^{-7}$ | 1135.5 | Ala(2.24), His(1.68), Val(1.00) |
| N—(((2',3'-Difluoro)-2-Phenyl) Acetyl)—HisTrpAlaVal<u>D</u>—AlaHis<u>D</u>—ProΨPhe—NH$_2$ | $3.61 \times 10^{-7}$ | 1103.4 | Ala(2.16), His(1.63), Val(1.00) |
| N—(((2',4'-Difluoro)-2-Phenyl) Acetyl)—HisTrpAlaVal<u>D</u>—AlaHis<u>D</u>—ProΨPhe—NH$_2$ | $1.80 \times 10^{-7}$ | 1103.2 | Ala(2.16), His(1.62), Val(1.00) |
| N—(((2',6'-Difluoro)-2-Phenyl) Acetyl)—HisTrpAlaVal<u>D</u>—AlaHis<u>D</u>—ProΨPhe—NH$_2$ | $5.71 \times 10^{-7}$ | 1103.2 | Ala(2.11), His(1.69), Val(1.00) |
| N—(((2-Amino)-2-Phenyl)Acetyl)—HisTrpAlaVal<u>D</u>—AlaHis<u>D</u>—ProΨPhe—NH$_2$ | $7.30 \times 10^{-9}$ | 1082.2 | N/A |
| N—(1-Naphthoyl)—HisTrpAlaVal<u>D</u>— | $1.81 \times 10^{-12}$ | 1103.9 | Ala(2.06), |

TABLE 1-continued

| STRUCTURE | IC$_{50}$(M) | MH$^+$(FAB)-MS | AAA |
|---|---|---|---|
| AlaHisD—ProΨPhe—NH$_2$ | | | His(2.12), Val(1.00) |
| N—(((3',4',5'-Trimethoxy)-3-Phenyl)Propionyl)—HisTrpAlaValD—AlaHisD—ProΨPhe—NH$_2$ | 1.11 × 10$^{-11}$ | 1171.8 | Ala(1.86), His(1.71), Val(1.00) |
| N—((6'-Methoxy)-2-(2-Naphthoyl)Propionyl)—HisTrpAlaValD—AlaHisD—ProΨPhe—NH$_2$ | 3.44 × 10$^{-11}$ | 1161.8 | Ala(1.87), His(1.87), Val(1.00) |
| N—(((3'-Trifluoromethyl)-3-Phenyl)Propionyl)—HisTrpAlaValD—AlaHisD—ProΨPhe—NH$_2$ | 3.47 × 10$^{-11}$ | 1149.8 | Ala(2.17), His(1.50), Val(1.00) |
| N—(((S)-3-Phenyl)Butyryl)—HisTrpAlaValD—AlaHisD—ProΨPhe—NH$_2$ | 5.47 × 10$^{-11}$ | 1095.9 | Ala(1.83), His(1.82), Val(1.00) |
| N—(((4'-Methoxy)-3-Phenyl)Propionyl)—HisTrpAlaValD—AlaHisD—ProΨPhe—NH$_2$ | 5.40 × 10$^{-12}$ | 1111.9 | Ala(1.84), His(1.76), Val(1.00) |
| N—((((S)-2-Hydroxy)-2-Phenyl)Acetyl)—HisTrpAlaValD—AlaHisD—ProΨPhe—NH$_2$ | 5.53 × 10$^{-9}$ | 1083.8 | Ala(1.92), His(1.64), Val(1.00.) |
| N—((3-Phenyl)Propionyl)—HisTrpAlaValD—AlaHisProΨPhe—NH$_2$ | 9.25 × 10$^{-9}$ | 1081.5 | Ala(1.80), His(1.75) Val(1.00) |
| N—((2-Methyl-2-Phenyl)Propionyl)—HisTrpAlaValD—AlaHisD—ProΨPhe—NH$_2$ | 1.46 × 10$^{-11}$ | 1095 | Ala(2.00), His(1.55), Val(1.00) |
| N—(3-(1-Naphthyl)Propionyl)—HisTrpAlaValD—AlaHisD—ProΨPhe—NH$_2$ | 1.77 × 10$^{-8}$ | 1131 | Ala(2.22), His(1.44), Val(1.00) |
| N—(((R)-3-Phenyl)Butyryl)—HisTrpAlaValD—AlaHisD—ProΨPhe—NH$_2$ | 9.12 × 10$^{-9}$ | 1095 | Ala(2.68), His(1.38), Val(1.00) |
| N—((9-Fluoroenoyl)1-Carbonyl)—HisTrpAlaValD—AlaHisD—ProΨPhe—NH$_2$ | 8.66 × 10$^{-9}$ | 1158 | Ala(2.71), His(1.08), Val(1.00) |
| N—(((2'-Methoxy)-3-Phenyl)Propionyl)—HisTrpAlaValD—AlaHisD—ProΨPhe—NH$_2$ | 9.00 × 10$^{-9}$ | 1111 | Ala(2.07), His(1.35), Val(1.00) |
| N—(((2',5'-Dimethoxy)-3-Phenyl)Propionyl)—HisTrpAlaValD—AlaHisD—ProΨPhe—NH$_2$ | 8.76 × 10$^{-9}$ | 1141.7 | Ala(2.23), His(1.67), Val(1.00) |
| N—((3-Phenyl)Propionyl)—HisTrpAlaValD—AlaHisD—ProΨTyr—NH$_2$ | 1.82 × 10$^{-8}$ | 1097.7 | N/A |
| N—(((2',3'-Dimethoxy)-3-Phenyl)Propionyl)—HisTrpAlaValD—AlaHisD—ProΨPhe—NH$_2$ | 3.50 × 10$^{-9}$ | 1141.7 | Ala(2.25), His(1.66), Val(1.00) |
| N—((3-Phenyl)Propionyl)—HisTrpAlaValD—AlaHis(3-(2-Pyrrolidinyl-3Hydroxy)Propionyl)—Phe—NH$_2$ | 1.76 × 10$^{-8}$ | 1139.6 | N/A |
| ((Isoquinolyly-Carbonyl)—HisTrpAlaValD—AlaHisD—ProΨPhe—NH$_2$ | 3.44 × 10$^{-9}$ | 1104.5 | Ala(1.82), His(1.32), Val(1.00) |
| N—((3-Phenyl)Propionyl)—HisTrpAlaΨValD—AlaHisD—ProΨPhe—NH$_2$ | 7.50 × 10$^{-8}$ | 1067.1 | Ala(1.00, His(3.17) |

---

We claim:
1. A compound of formula (I)

$$XX^1TrpX^2X^3X^4X^5X^6X^7NH_2 \quad \text{(I) (SEQ ID NO: 3)}$$

wherein

X is a group $X^8$Arg or D-Arg $X^9X^{10}$ and $X^8$ is des $NH_2$Pro,TyrPro,des $NH_2$TyrPro, Ada, Pro, D-Pro or is deleted;

$X^9$ is Gly, Ala, D-Ala or is deleted;

$X^{10}$ is Asn, Phe, D-Phe, or Phe or D-Phe substituted by one or more halo atoms;

or X is a group A—$(CH_2)$n—CO— in which A is a group containing 1 to 3 rings of which at least one ring is aromatic, each ring system being optionally substituted; and the alkylene group is optionally substituted by one to four groups selected from amino, hydroxy $C_{1-4}$ alkoxy and $C_{1-4}$ alkyl optionally substituted by halo and n is 0 to 4, or X is a group A—$(CH_2)$n—CO— in which A is an optionally substituted aromatic residue containing 1 to 3 rings and the alkylene group is optionally substituted by one to four groups selected from amino, $C_{1-4}$ alkoxy and $C_{1-4}$ alkyl optionally substituted by halo and n is 1 to 4, or X is cyclopentylcarbonyl substituted by a group $X^8$ Arg (or D-Arg) $X^9$ $X^{10}$ as hereinbefore defined;

$X^1$ is His, ThiAla or is deleted;

$X^2$ is Ala, D-Ala, CPenc, D-tBuGly or Pro;

$X^3$ is Val or Val substituted by one or more halo atoms;

$X^4$ is Gly, Ala, D-Ala, Sarcosine, Pro, D-Pro or D-Phe;

$X^5$ is His or ThiAla;

$X^6$ is D-Proψ, Proψ, 2-pyrrolidinyl-3-hydroxypropionyl or D-Pro; and $X^7$ is Nle,Leu,Phe,Val,Mox, D-Phe or Phe, or D-Phe substituted by one or more halo atoms or naphthylAla or naphthyl D-Ala or a hydrophobic, substituted aromatic amino acid or aralkylamine or is deleted;

or a pharmaceutically acceptable salt thereof.

2. The compound of claim 1 wherein X is a group A—$(CH_2)_n$—CO— in which A is phenyl, naphthyl, phenothiazinyl or indolyl optionally substituted by hydroxy, phenyl, halo, $C_{1-4}$ alkyl or $C_{1-4}$ alkoxy optionally substituted by halo; and n is 2.

3. The compound of claim 2 wherein A is phenyl or naphthyl optionally substituted by hydroxy, phenyl, halo, $C_{1-4}$ alkyl or $C_{1-4}$ alkoxy optionally substituted by halo; and n is 2.

4. The compound of claim 1 wherein $X^8$ is des $NH_2$TyrPro or des $NH_2$Pro; $X^9$ is Gly or D-Ala; $X^{10}$ is D-Phe; and n is 2.

5. The compound of claim 1 wherein said compound of formula (I) is

N-((R)-2-(6-Methoxy-2-Naphthyl)Propionyl)-HisTrpAlaValD-AlaHisD-ProψNle-$NH_2$;

N-((S)-2-(6-Methoxy-2-Naphthyl)Propionyl)-HisTrpAlaValD-AlaHisD-ProψNle-$NH_2$;

N-((S)-3-Phenylbutyryl)-HisTrpAlaValD-AlaHis D-ProψNle-$NH_2$;

N-((R)-3-Phenylbutyryl)-HisTrpAlaValD-AlaHis D-ProψNle-$NH_2$;

N-((3-Phenyl)Propionyl)-HisTrpAlaVal D-Ala(3-(2-Thi)-Ala)D-ProψNle-$NH^2$;

N-((S)-3,3,3-Trifluoro-2-Methoxy-2-Phenyl-Propionyl)-HisTrpAlaValD-ProψNle-$NH^2$;

N-((R)-3,3,3-Trifluoro-2-Methoxy-2-Phenyl-Propionyl)-HisTrpAlaValD-ProψNle-$NH_2$;

N-3-(((4'-Hydroxy)Phenyl)Propionyl)-ProD-ArgGly D-PheHisTrpAlaValGly-HisD-ProψNle-$NH_2$;

N-(((4'Hydroxy)-3-Phenyl)Propionyl)-Pro D-ArgHisTrpAlaValD-AlaHisD-ProLeu-$NH_2$;

N-((3-Phenyl)Propionyl)-HisTrpAlaValD-AlaHis D-Proψmox-$NH_2$;

N-((3-Phenyl)Propionyl)-HisTrpAlaValD-ProψPhe-$NH_2$;

N-((3-Phenyl)Propionyl)-TrpAlaValD-AlaHis D-ProψLeu-$NH_2$;

N-((3-Phenyl)Propionyl)-HisTrpProValD-ProHis D-ProψLeu-$NH_2$;

N-3-(((3'-Trifluoromethyl)Phenyl)Propionyl)-HisTrpAlaValD-AlaHisD-ProψLeu-$NH_2$;

N-((3-Phenyl)Propionyl)-(3-(2-Thi)-Ala)TrpAlaVal D-AlaHisD-ProψLeu-$NH_2$;

N-((deamino-Pro)-D-ArgD-Ala D-PheHisTrpAlaValGlyHisD-ProψNle-$NH_2$;

N-((3-Phenyl)Propionyl)-HisTrpAlaValGlyHis D-ProψNle-$NH_2$;

N-((deamino-Pro)-D-ArgD-AlaD-PheHisTrpAlaVal D-AlaHisD-ProψNle-$NH_2$;

N-((3-Phenyl)Propionyl)-HisTrpAlaValD-AlaHis D-ProψNle-$NH_2$;

TyrProD-ArgGlyD-PheHisTrpAlaValGlyHis D-ProψNle-$NH_2$;

D-ArgGlyD-PheHisTrpAlaValGlyHisD-ProψNle-$NH_2$;

N-((3-Phenyl)Propionyl)-HisTrpAlaValD-AlaHis D-ProPhe-$NH_2$;

N-((3-Phenyl)Propionyl)-HisTrpAlaValD-AlaHis D-Proψ(3-(2-Naphthyl)-D-Ala)-$NH_2$;

N-((3-Phenyl)Propionyl)-HisTrpAlaValD-PheHis D-ProψPhe-$NH_2$;

D-PheHisTrpAlaValD-AlaHisD-ProψPhe-$NH_2$;

N-((3-Phenyl)Propionyl)-D-ProArgGly D-PheHisTrpAlaValD-AlaHisD-ProψPhe-$NH_2$;

N-((3-Phenyl)Propionyl)-(3-(2-Thi)-Ala)-TrpAlaVal D-AlaHisD-ProψPhe-$NH_2$;

N-((3-Phenyl)Propionyl)-HisTrpAlaVal-(Sarcosine)-His
 D-ProψPhe-NH$_2$;
N-3-(((4'-Hydroxy)Phenyl)Propionyl)-HisTrpAlaVal
 D-AlaHisD-ProψPhe-NH$_2$;
N-(((2',6'-Dichloro)-2-Phenyl)Acetyl)-HisTrpAlaVal
 D-AlaHisD-ProψNle-NH$_2$;
N(((3',4'-Dichloro)-2-Phenyl)Acetyl)-HisTrpAlaValD-
 AlaHisD-ProψNle-NH$_2$;
N-(((4'-Hydroxy)-2-Phenyl)Acetyl)-HisTrpAlaVal
 D-AlaHisD-ProψNle-NH$_2$;
N-(1-Naphthoyl)-HisTrpAlaValD-AlaHis
 D-ProψNle-NH$_2$;
N-((3,7-Dihydroxy)-2-Naphthoyl)-HisTrpAlaVal
 D-AlaHisD-ProψNle-NH$_2$;
N-((3,4-Dihydroxy)-2-Phenyl)Acetyl)-HisTrpAlaVal
 D-AlaHisD-ProψNle-NH$_2$;
N-(2-(3-Pyridyl)Acetyl)-HisTrpAlaValD-AlaHis
 D-ProψNle-NH$_2$;
N-(2-(2-Thienyl)Acetyl)-HisTrpAlaValD-AlaHis
 D-ProψNle-NH$_2$;
N-(((3-Fluoro)-3-Phenyl)Prop-ionyl)-HisTrpAlaVal
 D-AlaHisD-ProψNle-NH$_2$;
N-(((4-hydroxy-3-methoxy)-2-Phenyl)Acetyl)-HisTrpA-
 laValD-AlaHisD-ProψNle-NH$_2$;
N-(((R)-(−)-2-Phenyl)Propionyl)-HisTrpAlaValD-AlaHis
 D-ProψPhe-NH$_2$;
N-(((S)-(+)-2-Phenyl)Propionyl)-HisTrpAlaValD-AlaHis
 D-ProψPhe-NH$_2$;
N-(((Trans)-2-Phenyl)-Cyclopropanoyl)-HisTrpAlaVal
 D-AlaHisD-ProψPhe-NH$_2$;
N-(3-(10-Phenothiazinyl)Propionyl-HisTrpAlaVal
 D-AlaHisD-ProψPhe-NH$_2$;
N-((3-Methyl-3-Phenyl)Butyryl)-HisTrpAlaValD-AlaHis
 D-ProψPhe-NH$_2$;
N-(((2'-Trifluoromethyl)-2-Phenyl)Acetyl)-HisTrpAlaVal
 D-AlaHisD-ProψPhe-NH$_2$;
N-(((3'-Trifluoromethyl)-2-Phenyl)Acetyl)-HisTrpAlaVal
 D-AlaHisD-ProψPhe-NH$_2$;
N-(((4'-Trifluoromethyl)-2-Phenyl)Acetyl)-HisTrpAlaVal
 D-AlaHisD-ProψPhe-NH$_2$;
N-(((2',3'-Difluoro)-2-Phenyl)Acetyl)-HisTrpAlaVal
 D-AlaHisD-ProψPhe-NH$_2$;
N-(((2',4'-Difluoro)-2-Phenyl)Acetyl)-HisTrpAlaVal
 D-AlaHisD-ProψPhe-NH$_2$;
N-(((2',6'-Difluoro)-2-Phenyl)Acetyl)-HisTrpAlaVal
 D-AlaHisD-ProψPhe-NH$_2$;
N-(((2-Amino)-2-Phenyl)Acetyl)-HisTrpAlaVal
 D-AlaHisD-ProψPhe-NH$_2$;
N-(1-Naphthoyl)-HisTrpAlaValD-AlaHis
 D-ProψPhe-NH$_2$;
N-(((3',4',5'-Trimethoxy)-3-Phenyl)Propionyl)-HisTrpA-
 laValD-AlaHisD-ProψPhe-NH$_2$;
N-((6'-Methoxy)-2-(2-Naphthoyl)Propionyl)-HisTrpAla-
 ValD-AlaHisD-ProψPhe-NH$_2$;
N-(((3'-Trifluoromethyl)-3-Phenyl)Propionyl)-HisTrpA-
 laValD-AlaHisD-ProψPhe-NH$_2$;
N-(((S)-3-Phenyl)Butyryl)-HisTrpAlaValD-AlaHis
 D-ProψPhe-NH$_2$;
N-(((4'-Methoxy)-3-Phenyl)Propionyl)-HisTrpAlaVal
 D-AlaHisD-ProψPhe-NH$_2$;
N-((((S)-2-Hydroxy)-2-Phenyl)Acetyl)-HisTrpAlaVal
 D-AlaHisD-ProψPhe-NH$_2$;
N-((3-Phenyl)Propionyl)-HisTrpAlaVal
 D-AlaHisProψPhe-NH$_2$;
N-((2-Methyl-2-Phenyl)Propionyl)-HisTrpAlaVal
 D-AlaHisD-ProψPhe-NH$_2$;
N-(3-(1-Naphthyl)Propionyl)-HisTrpAlaValD-AlaHis
 D-ProψPhe-NH$_2$;
N-(((R)-3-Phenyl)Butyryl)-HisTrpAlaValD-AlaHis
 D-ProψPhe-NH$_2$;
N-((9-Fluoroenoyl)1-Carbonyl)-HisTrpAlaValD-AlaHis
 D-ProψPhe-NH$_2$;
N-(((2'-Methoxy)-3-Phenyl)Propionyl)-HisTrpAlaVal
 D-AlaHisD-ProψPhe-NH$_2$;
N-(((2',5'-Dimethoxy)-3-Phenyl)Propionyl)-HisTrpAla-
 ValD-AlaHisD-ProψPhe-NH$_2$;
N-((3-Phenyl)Propionyl)-HisTrpAlaValD-AlaHis
 D-ProψTyr-NH$_2$;
N-(((2',3'-Dimethoxy)-3-Phenyl)Propionyl)-HisTrpAla-
 ValD-AlaHisD-ProψPhe-NH$_2$;
N-((3-Phenyl)Propionyl)-HisTrpAlaVal
 D-AlaHis(3-(2-Pyrrolidinyl-3-Hydroxy)Propionyl)-Phe-NH$_2$;
((Isoquinolylcarbonyl)-HisTrpAlaValD-AlaHis
 D-ProψPhe-NH$_2$; or
N-((3-Phenyl)Propionyl)-HisTrpAlaValD-AlaHis
 D-ProψPhe-NH$_2$;
or a pharmaceutically acceptable salt thereof.

6. The compound of claim 5 wherein said compound of formula (I) is

N-((3-Phenyl)Propionyl)-HisTrpAlaValD-AlaHis
 D-ProψPhe-NH$_2$;
N-3-(((4'-Hydroxy)Phenyl)Propionyl)-HisTrpAlaVal
 D-AlaHisD-ProψPhe-NH$_2$;
N-(1-Naphthoyl)-HisTrpAlaValD-AlaHis
 D-ProψPhe-NH$_2$;
N-(((4'-Methoxy)-3-Phenyl)Propionyl)-HisTrpAlaVal
 D-AlaHisD-ProψPhe-NH$_2$;
N-(((S)-3-Phenyl)Butyryl)-HisTrpAlaValD-AlaHis
 D-ProψPhe-NH$_2$;
N-(((R)-(−)-2-Phenyl)Propionyl)-HisTrpAlaValD-AlaHis
 D-ProψPhe-NH$_2$;
N-(((3'-Trifluoromethyl)-3-Phenyl)Propionyl)-HisTrpA-
 laValD-AlaHisD-ProψPhe-NH$_2$;
N-(((Trans)-2-Phenyl)-Cyclopropanoyl)-HisTrpAlaVal
 D-AlaHisD-ProψPhe-NH$_2$;
N-(((3',4',5'-Trimethoxy)-3-Phenyl)Propionyl)-HisTrpA-
 laValD-AlaHisD-ProψPhe-NH$_2$; or
N-((2-Methyl-2-Phenyl)Propionyl)-HisTrpAlaVal
 D-AlaHisD-ProψPhe-NH$_2$;
or a pharmaceutically acceptable salt thereof.

7. A pharmaceutical composition comprising a compound of formula (I)

$$XX^1TrpX^2X^3X^4X^5X^6X^7NH_2 \qquad \text{(I) (SEQ ID NO: 3)}$$

wherein

X is a group $X^8Arg$(or D-Arg)$X^9X^{10}$
 and $X^8$ is des NH$_2$Pro,TyrPro,des NH$_2$TyrPro, Ada, Pro, D-Pro or is deleted;
$X^9$ is Gly, Ala, D-Ala or is deleted;
$X^{10}$ is Asn, Phe, D-Phe, or Phe or D-Phe substituted by one or more halo atoms;
or X is a group A—(CH$_2$)n—CO— in which A is a group containing 1 to 3 rings of which at least one ring is aromatic, each ring system being optionally substituted; and the alkylene group is optionally substituted by one to four groups selected from amino, hydroxy $C_{1-4}$ alkoxy and $C_{1-4}$ alkyl optionally substituted by halo and n is 0 to 4, or X is a group A—(CH$_2$)n—CO— in which A is an optionally substituted aromatic residue containing 1 to 3 rings and the alkylene group is optionally substituted by one to four groups selected from amino, $C_{1-4}$ alkoxy and $C_{1-4}$ alkyl optionally substituted by halo and n is 1 to 4, or X is cyclopentylcarbonyl substituted by a group $X^8$ Arg (or D-Arg) $X^9$ $X^{10}$ as hereinbefore defined;

$X^1$ is His, ThiAla or is deleted;

$X^2$ is Ala, D-Ala, CPenc, D-tBuGly or Pro;

$X^3$ is Val or Val substituted by one or more halo atoms;

$X^4$ is Gly, Ala, D-Ala, Sarcosine, Pro, D-Pro or D-Phe;

$X^5$ is His or ThiAla;

$X^6$ is D-Proψ, Proψ, 2-pyrrolidinyl-3-hydroxypropionyl or D-Pro; and $X^7$ is Nle,Leu,Phe,Val,Mox, D-Phe or Phe, or D-Phe substituted by one or more halo atoms or naphthylAla or naphthyl D-Ala or a hydrophobic, substituted aromatic amino acid or aralkylamine or is deleted;

or a pharmaceutically acceptable salt thereof; and at least one pharmaceutical carrier and optionally, one or more other pharmaceutically active agents therewith.

8. The pharmaceutical composition of claim 7 wherein said compound of formula (I) is N-((3-Phenyl)Propionyl)-HisTrpAlaValD-AlaHis D-ProψPhe-NH$_2$;

N-3-(((4'-Hydroxy)Phenyl)Propionyl)-HisTrpAlaVal D-AlaHisD-ProψPhe-NH$_2$;

N-(1-Naphthoyl)-HisTrpAlaValD-AlaHis D-ProψPhe-NH$_2$;

N-(((4'-Methoxy)-3-Phenyl)Propionyl)-HisTrpAlaVal D-AlaHisD-ProψPhe-NH$_2$;

N-(((S)-3-Phenyl)Butyryl)-HisTrpAlaValD-AlaHis D-ProψPhe-NH$_2$;

N-(((R)-(−)-2-Phenyl)Propionyl)-HisTrpAlaValD-AlaHis D-ProψPhe-NH$_2$;

N-(((3'-Trifluoromethyl)-3-Phenyl)Propionyl)-HisTrpAlaValD-AlaHisD-ProψPhe-NH$_2$;

N-(((3',4',5'-Trimethoxy)-3-Phenyl)Propionyl)-HisTrpAlaValD-AlaHisD-ProψPhe-NH$_2$;

N-(((Trans)-2-Phenyl)-Cyclopropanoyl)-HisTrpAlaVal D-AlaHisD-ProψPhe-NH$_2$; or

N-((2-Methyl-2-Phenyl)Propionyl)-HisTrpAlaVal D-AlaHisD-ProψPhe-NH$_2$;

or a pharmaceutically acceptable salt thereof; and at least one pharmaceutical carrier and optionally, one or more other pharmaceutically active agents therewith.

\* \* \* \* \*